United States Patent [19]
Love et al.

[11] Patent Number: 5,507,919
[45] Date of Patent: Apr. 16, 1996

[54] APPARATUS FOR THE THERMAL AND CATALYTIC DEFLUORINATION OF ALKYLATE

[75] Inventors: Scott D. Love; Stone P. Washer, both of Bartlesville, Okla.

[73] Assignee: Phillips Petroleum Company, Bartlesville, Okla.

[21] Appl. No.: 283,432

[22] Filed: Aug. 1, 1994

Related U.S. Application Data

[62] Division of Ser. No. 979,988, Nov. 23, 1992, Pat. No. 5,367,115.

[51] Int. Cl.$^6$ ............................... B01D 3/16; C07C 2/62
[52] U.S. Cl. ..................... 202/158; 202/153; 196/105; 196/130; 203/28; 203/29; 203/39; 203/41; 203/98; 203/DIG. 6; 203/DIG. 19; 203/DIG. 25
[58] Field of Search ..................... 202/153, 158, 202/176, 178; 203/DIG. 19, 28, DIG. 6, 29, 41, DIG. 25, 39, 98; 196/105, 116, 130; 585/723, 713, 728, 802

[56] References Cited

U.S. PATENT DOCUMENTS

| | | |
|---|---|---|
| 2,729,588 | 1/1956 | Hannah . |
| 2,769,853 | 11/1956 | Hettick . |
| 2,984,693 | 5/1961 | Cabbage . |
| 3,019,273 | 1/1962 | DeLano . |
| 3,403,080 | 9/1968 | Clay .......................................... 203/39 |
| 4,720,327 | 1/1988 | Aguila et al. ..................... 203/DIG. 25 |
| 5,296,104 | 3/1994 | Signorini et al. ................. 203/DIG. 19 |
| 5,367,115 | 11/1994 | Love et al. ............................... 585/723 |

FOREIGN PATENT DOCUMENTS 705462 3/1965 Canada ................................... 585/723

Primary Examiner—Wilbur Bascomb, Jr.
Attorney, Agent, or Firm—Ryan N. Cross

[57] ABSTRACT

An apparatus and method are provided for the defluorination of a liquid hydrocarbon mixture, containing organic fluorides, produced during the conversion of hydrocarbons using a fluorine-containing catalyst. In one embodiment, both a thermal means and a contacting material are used to effectuate a more complete defluorination. The liquid hydrocarbon mixture is extracted from a distillation column and heated sufficiently in the thermal means to decompose at least some of the organic fluorides. The effluent from the thermal means is separated into a vaporous and a liquid effluent. The liquid effluent is passed to the bottom of the distillation column where it undergoes further defluorination through contact with the contacting material.

10 Claims, 3 Drawing Sheets

APPARATUS FOR THE THERMAL AND CATALYTIC DEFLUORINATION OF ALKYLATE

This application is a Division of application Ser. No. 07/979,988 filed on Nov. 23, 1992 now U.S. Pat. No. 5,367,115.

This invention relates to the defluorination of the reaction product of conversion processes utilizing a fluorine-containing catalyst.

In the alkylation of low-boiling paraffinic hydrocarbons with alkylating reactants to form normally liquid paraffins having high octane numbers, hydrofluoric acid finds perhaps its most important use as a catalyst. It is in such alkylation processes that the subject invention finds particular utility; however, it should be understood that it is not limited thereto but can be employed in any other hydrocarbon conversion process where it is desired to thermally decompose organic fluoride compounds contained in reaction products.

In such alkylation processes, low-boiling paraffinic hydrocarbons, particularly isobutane and/or isopentane and alkylating agents, particularly low-boiling olefins such as propylene, various butylenes, and/or various amylenes or the corresponding alkyl fluorides are intimately contacted in liquid phase at temperatures between about 50° F. and about 150° F., with liquid concentrated hydrofluoric acid. The reaction periods range from about 0.2 to about 30 minutes, and thereafter the reaction effluents are passed to a settling zone for separation into a liquid hydrocarbon phase and a liquid acid phase. A large portion of the liquid hydrofluoric acid phase from this settling zone is generally recycled to the reaction zone while some is withdrawn and subject to purification for the removal of water and acid-soluble organic impurities. The hydrocarbon phase from the settling zone is generally subjected to fractional distillation to remove hydrogen fluoride dissolved therein, which is generally present to the extent of about 0.5 to about 3 percent by volume, and to separate various hydrocarbon fractions which may comprise unreacted isobutane, unreacted normal butane and one or more alkylate fractions. This invention is primarily concerned with the removal of the hydrogen fluoride from the hydrocarbon phase and the defluorination of the alkylate fractions from the primary fractionator.

While hydrogen fluoride can be readily separated from the alkylate by the above-mentioned processes of phase separation and fractionation, the organic fluorides which form during the reaction pose a more difficult separation problem.

In conventional alkylation processes, the organic fluoride compounds contained in the alkylate fraction are decomposed by thermal means such as by an external reboiler, hydrogen fluoride vapors being recoverable and reboiler heat being used to supply heat to the primary fractionator. Although this type of thermal defluorination is generally satisfactory, the conditions are such that a small but significant amount of organic fluorides are still not decomposed and are carried along with the alkylate fraction. Additionally, either such processes have allowed some of the alkylate fraction to bypass the reboiler and, thus, the organic fluoride compounds contained therein are not decomposed; or they have not allowed for any of the alkylate fraction to pass more than once through the reboiler and, thus, have not allowed unconverted fluorides to get a second chance at thermal decomposition.

Accordingly, an object of this invention is to provide an improved method and apparatus for defluorinating the reaction products in a hydrocarbon conversion process, such as an alkylation process, by improving thermal decomposition of the organic fluoride compounds present in the alkylate fraction.

Another object of this invention is to provide an improved method and apparatus for defluorinating the reaction products in a hydrocarbon conversion process by using both thermal and chemical decomposition means.

A further object of this invention is to provide a method of defluorination in a hydrocarbon conversion process which will result in material savings in the maintenance cost for the equipment used for purifying the alkylate fraction.

Other objects and advantages of this invention will become apparent to those skilled in the art from the following description and the accompanying drawings.

The above objects are realized in an apparatus and a process for defluorinating a liquid hydrocarbon mixture containing organic fluorides wherein the liquid hydrocarbon mixture is introduced through an inlet to a vertically extended distillation column containing a vertical series of trays above and below the inlet such that the liquid hydrocarbon mixture flows generally downward; the liquid hydrocarbon mixture is maintained in the distillation column at a temperature above vaporizing temperature of hydrogen fluoride and low-boiling hydrocarbons under the existing pressure such that the hydrogen fluoride and low-boiling hydrocarbons separate from said liquid hydrocarbon mixture and flow generally upward in countercurrent contact with the downward flowing liquid hydrocarbon mixture; liquid hydrocarbon mixture is withdrawn from the distillation column below the inlet; the thus withdrawn liquid hydrocarbon mixture is passed to a heating means where the liquid hydrocarbon is heated sufficiently to cause some of the organic fluorides in the liquid hydrocarbon mixture to decompose, producing a vaporous effluent containing hydrogen fluoride and leaving a liquid effluent containing less organic fluorides than the liquid hydrocarbon introduced into the heating means; said vaporous effluent and said liquid effluent are passed to a phase separation zone wherein said vaporous effluent separates from said liquid effluent, the vaporous effluent is introduced to the distillation column below the inlet so that the hydrogen fluoride vapors flow upward and are in countercurrent contact with the downward flowing liquid hydrocarbon mixture; the liquid effluent is withdrawn from the phase separation zone and split into two streams, with one stream being returned to the heating means for further thermal decomposition of organic fluorides.

According to another aspect of the invention there is provided an apparatus and process for the defluorination of a liquid hydrocarbon mixture containing organic fluorides produced during the conversion of hydrocarbons using a fluorine-containing catalyst wherein said liquid hydrocarbon mixture is introduced into a distillation column to separate a vaporous fraction containing hydrogen fluoride and low-boiling hydrocarbons from a liquid fraction containing dissolved organic fluorides, the liquid fraction is withdrawn from the distillation column and introduced into a first defluorination zone wherein at least a portion of the organic fluorides are thermally decomposed, forming a vaporous effluent containing hydrogen fluoride and leaving a liquid effluent containing less dissolved organic fluorides than the liquid fraction introduced into the first defluorination zone. The vaporous fraction is passed to the lower section of the distillation column and at least a first portion of the liquid effluent is passed to a second defluorination zone. The first portion of the liquid effluent is passed through a contacting material located within the second defluorination zone and then is withdrawn as net product.

DETAILED DESCRIPTION

Figure 1:
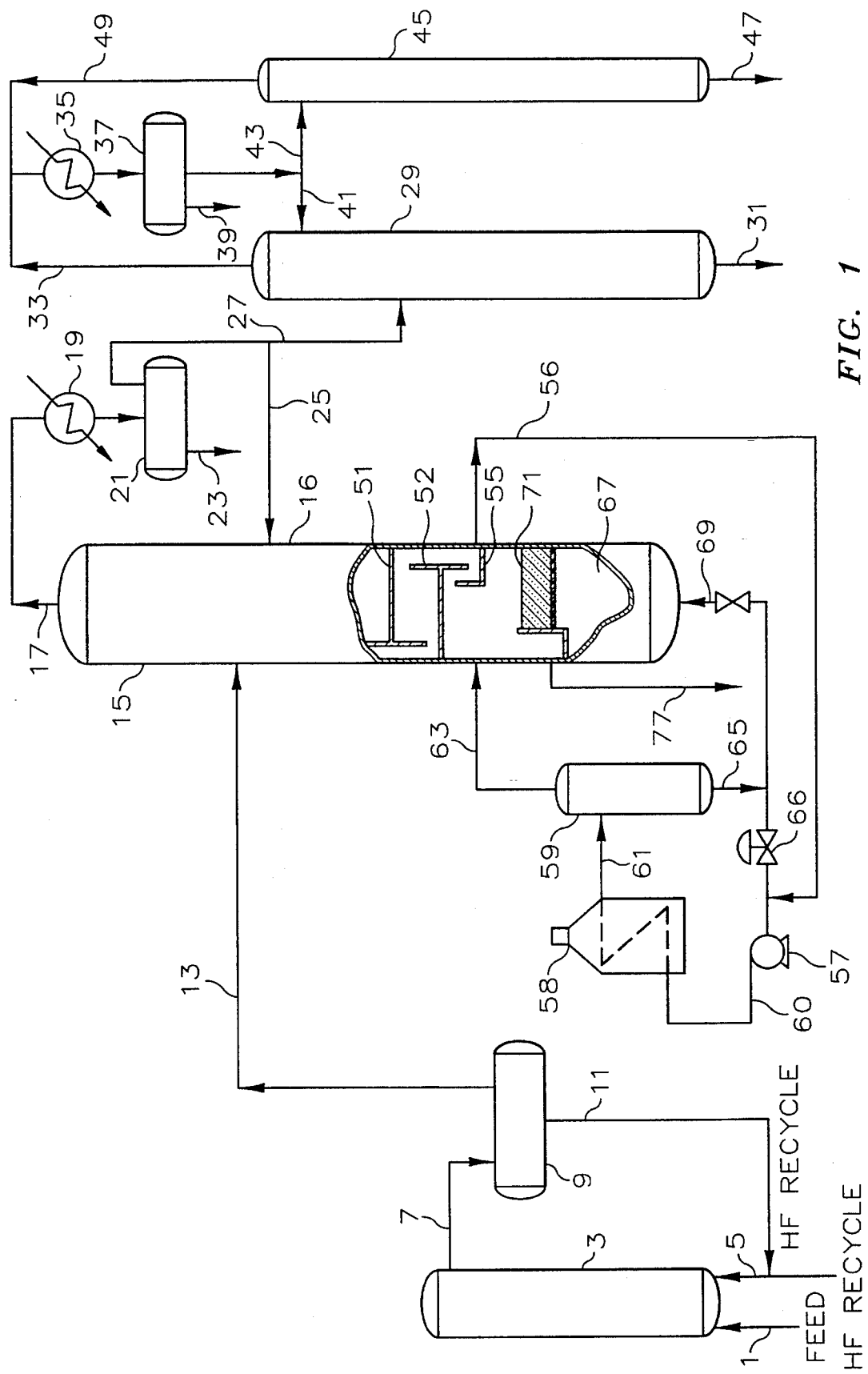
FIG. 1 is a diagrammatic illustration of an alkylation process utilizing the present invention.

Referring now to the drawings, in particular, FIG. 1, an alkylation process in illustrated which utilizes the present invention. Low boiling paraffinic hydrocarbons such as isobutane and propane and alkylating reactants such as butylene and propylene are introduced via line 1 into alkylator 3. A fluorine-containing catalyst, typically hydrofluoric acid catalyst, is introduced into alkylator 3 through line 5 where it is intimately mixed with the hydrocarbon feed. The conditions of temperature, pressure and reaction time as well as the ratios of paraffinic hydrocarbon to olefin and hydrocarbon to acid are well known in the art. For example, the mole ratio of isobutane to olefin in the total feed can be between about 1.5:1 and about 12:1, usually about 5:1. The ratio of hydrocarbon to acid catalyst will generally be about 0.5:1 to about 10:1 on a liquid volume basis. The reactants are intimately contacted with the acid catalyst in the alkylator 3 at temperatures between about 50° F. and about 150° F. and at a pressure sufficient to maintain the reactants in a liquid phase for a residence time of about 0.2 to about 30 minutes.

After a suitable contact period the reaction mixture is passed from alkylator 3 through conduit 7 to a phase separator or acid settler 9 wherein a phase separation between the liquid hydrocarbon mixture phase and the liquid hydrofluoric acid phase is readily carried out by settling. The acid phase is recycled via conduit 11 to the alkylator 3. While the flow diagram shows a direct course for this recycle acid, it should be understood that intermediate purification steps can be employed if desired.

The lighter or liquid hydrocarbon mixture phase from the phase separator 9 is passed via conduit 13 into a primary fractionator 15, such as a distillation column. A vaporous fraction comprising a low-boiling mixture of hydrofluoric acid and low-boiling hydrocarbons, such as propane and isobutane, is passed overhead through conduit 17 and after being cooled in cooler 19 enters accumulator 21 as a liquid. In accumulator 21, the mixture separates into an acid phase and a hydrocarbon phase, and the acid phase returns to the system via conduit 23. The hydrocarbon phase is withdrawn from accumulator 21 through conduit 25 and a portion thereof is recycled to primary fractionator 15 while the remainder is charged to a depropanizer 29 through conduit 27. From the bottom of depropanizer 29, a stream, comprising mainly isobutane, is taken off through conduit 31 and recycled to the alkylator 3. A mixture comprising hydrogen fluoride and propane is passed overhead from the depropanizer 29 through line 33, and thereafter is passed through cooler 35 into accumulator 37. In accumulator 37, the mixture separates into an acid phase and a hydrocarbon phase, the acid phase being returned to the system through line 39. The hydrocarbon phase is withdrawn from accumulator 37 through line 41 and a portion thereof is recycled to depropanizer 29 while the remainder is introduced via line 43 into stripper 45. From the bottom of stripper 45, a stream of propane is taken off through line 47 while the overhead, comprising a mixture of hydrogen fluoride and propane, is passed by means of line 49 through cooler 35 into accumulator 37.

Figure 2:
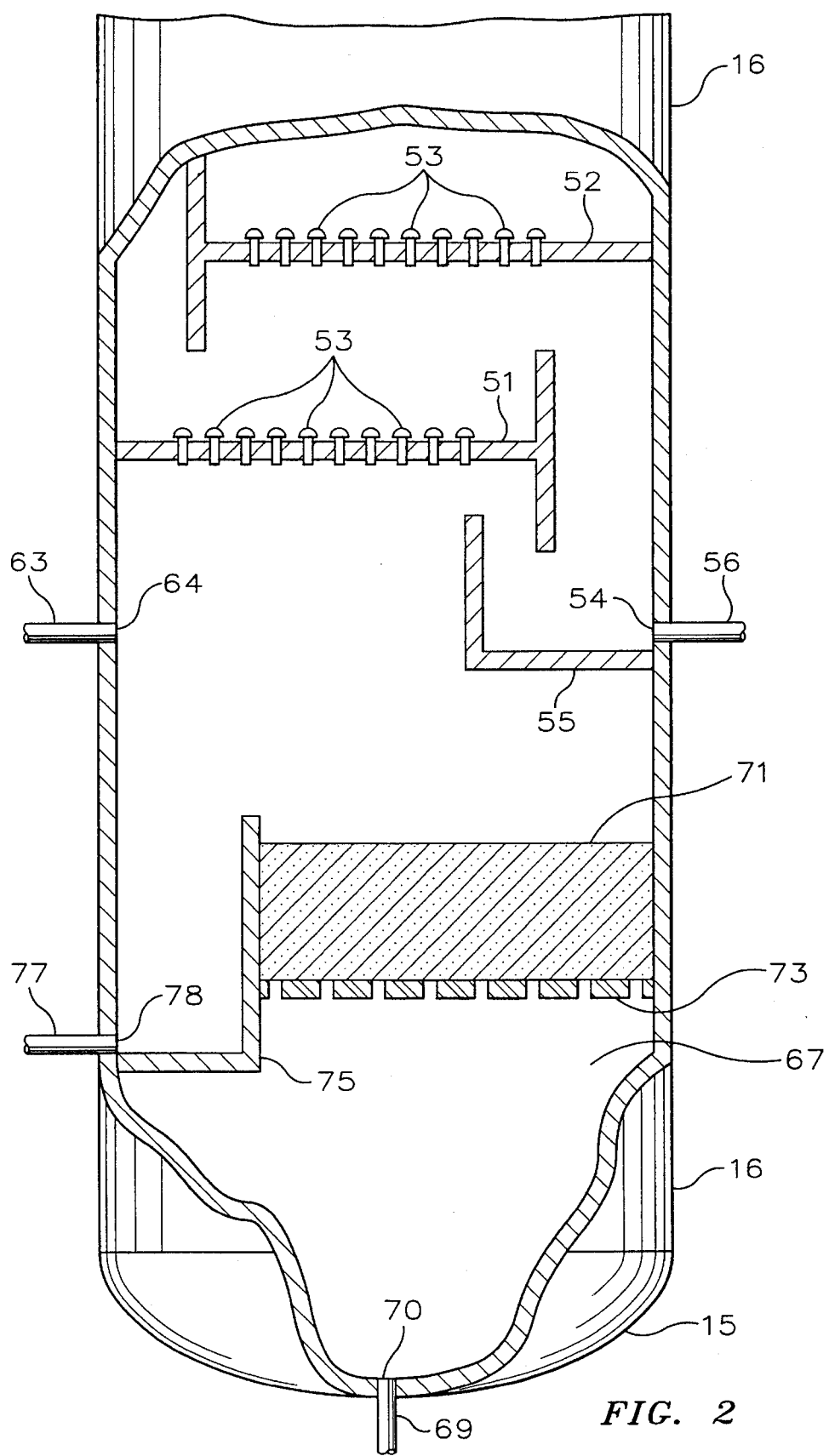
FIG. 2 is an isometric illustration of the lower section of a distillation column with features suitable for use in the present invention.
Figure 3:
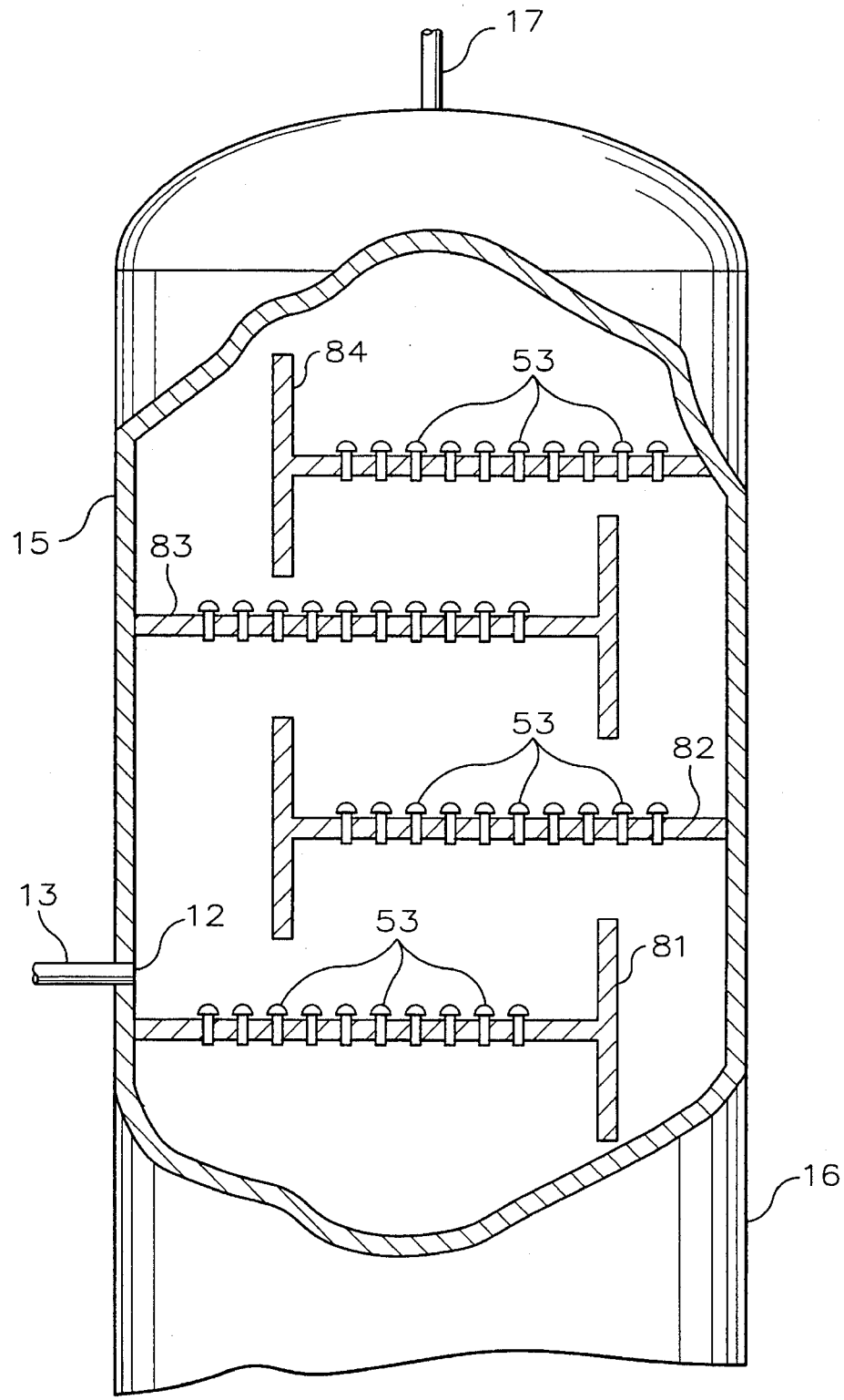
FIG. 3 is an isometric illustration of the upper section of a distillation column with features suitable for use in the present invention.

Referring again to primary fractionator 15, which can be seen in more detail in FIGS. 2 and 3, this fractionator is shown in the form of a vertically extended distillation column. The distillation column illustrated in the Figures comprises a vertically elongated container 16 containing vapor liquid contacting trays, such as bubble-cap trays, sieve trays, plate trays, etc., some of which, trays 51, 52, and 81–84 are shown in the bottom and top sections of the fractionator in FIGS. 2 and 3, respectively. The trays are shown having bubble caps 53 which allow upward moving vapors, in this case the vaporous fraction described above, to flow in countercurrent contact with downward flowing liquids, in this case the liquid hydrocarbon mixture introduced to the distillation column via line 13. Referring again to FIG. 1, a trap-out tray 55, or the like, is located in the bottom section of the fractionator below the array of vapor-liquid contacting trays and from this bottom trap-out tray the liquid fraction, comprising heavy and tight alkylates, unreacted isobutane, normal butane, and undesirable hydrocarbon-soluble organic fluoride compounds, is withdrawn from fractionator 15 through outlet 54 via conduit 56. The major portion of the liquid fraction withdrawn from fractionator 15 flows through pump 57 via conduit 56 and is sent via conduit 60 from pump 57 to a suitable heating means 58, preferably an indirect heat exchange means, such as a direct fired reboiler, which along with phase separation chamber 59, functions as a defluorinization zone. Alternatively, instead of a direct fired reboiler, any simple heat exchanger can be employed using steam, Dowtherm®, or another heat transfer material. In heating means 58 the liquid fraction is heated to from a heated effluent which is sent to phase separator 59 via line 61. In phase separator 59 the heated effluent is separated into a vaporous effluent and a liquid effluent.

The vaporous effluent containing hydrogen fluoride is withdrawn from phase separator 59 via line 63 and is passed through inlet 64 into the lower section of the primary fractionator 15, preferably at a point below the lower-most conventional tray 51. The liquid effluent from phase separator 59, containing less organic fluorides than the fraction sent to the heating means 58, is withdrawn from phase separator 59 via line 65. The liquid effluent is split with a first portion of the liquid effluent being charged to the kettle 67 through inlet 70 via line 69. The second portion of the liquid effluent flows through pump 57 and returns to the heating means 58 through conduit 60. Flow of the second portion through conduit 60 is controlled by valve means 66.

Referring now to FIG. 2, it can be seen that as liquid effluent collects in kettle 67, the tops of the liquid effluent in kettle 67 are forced through contacting material 71 by the pressure of liquid effluent coming in through line 69. Contacting material 71 can be supported on a shelf 73 with suitable holes of predetermined diameter to allow the liquid effluent to pass.

The contacting material 71 is in fluid flow communication with trap-out tray 75, such that the defluorinated fraction having passed through contact material 71, overflows the contact material 71 into trap-out tray 75. The defluorinated fraction in the trap-out tray 75 is removed through outlet 78 via conduit 77 as net defluorinated product.

In operation, the liquid hydrocarbon mixture enters primary fractionator 15 from conduit 13 through inlet 12. The liquid hydrocarbon mixture collects in the tray 81 eventually overflowing from the tray 81 into a lower tray. The liquid hydrocarbon mixture then collects in that lower tray and eventually overflows into the next lower tray. This process of overflow from higher tray to lower tray continues throughout the series of trays until the liquid hydrocarbon mixture in tray 51 overflows into trap-out tray 55 where it is withdrawn from the system.

Primary fractionator 15 is, generally, maintained at a temperature above the vaporizing temperature of hydrogen fluoride and low-boiling hydrocarbons under the existing pressure. Thus, while the liquid hydrocarbon mixture introduced into the primary fractionator 15 through conduit 13 generally flows downward, hydrogen fluoride and low-boiling hydrocarbons vaporize out of the liquid hydrocarbon mixture forming the vaporous fraction and leaving the downward flowing liquid fraction. The vaporous fraction flows generally upward through the bubbles in the bubble trays in counter-current contact with the downward flowing liquids. Additional hydrogen fluoride and light hydrocarbons from phase separator 59 enter the primary fractionator 15 through conduit 63 and also flows upward in counter-current contact with the downward flowing liquids. Generally, some of the liquid fraction is carried upward with the vaporous fraction. Most of this carried liquid fraction collects in the upper-most trays 82, 83 and 84, and returns to flowing generally downward in the manner previously described.

Thus, the vaporous fraction passed overhead through conduit 17 consists essentially of a low-boiling mixture of hydrofluoric acid and low-boiling hydrocarbons, such as propane and isobutane, and the liquid fraction withdrawn through conduit 56 consists essentially of heavy and light alkylates, unreacted isobutane, normal butane, and hydrocarbon-soluble organic fluorides.

The liquid fraction withdrawn from the primary fractionator via conduit 56 is passed to the heating means 58. In the heating means 58, operated from about 350° F. to about 500° F. preferably from 400° F. to 450° F., and in the phase separator 59, products of organically combined fluorine predominantly in the $C_3$–$C_4$ range, such as isopropyl fluoride and butyl fluoride, are thermally decomposed to release hydrogen fluoride and vaporized light hydrocarbons. This thermal defluorination results in a substantially defluorinated liquid effluent from phase separator 59. Typically, the liquid effluent will be about 85% to about 95% defluorinated after from about 10 minutes to about 30 minutes. At least a portion of this liquid effluent is passed to the kettle 67 of primary fractionator 15 where it is contacted with the contacting material and, thus, undergoes further defluorination by this contact. Additionally, further thermal defluorination may occur while the liquid effluent resides in Kettle 67.

Thus, the kettle and contacting material define a second defluorination zone where liquid hydrocarbons are further defluorinated by contact with the contacting material. Although the second defluorination zone could be located outside the kettle of the distillation column, this arrangement would not have the advantage of the arrangement shown in the Figures of using the liquid effluent to supply heat to maintain a suitable temperature within the distillation column. Additionally, vaporous effluent passed via line 63 into the primary fractionator also serves to supply heat to the primary fractionator.

While any suitable material that will aid in the defluorination of the organic fluorides can be used as the contacting material, carbon has been found to be especially suitable and preferably the contacting material is activated carbon.

Modifications and variations of the present invention are possible in light of the above teachings; therefore, it is to be understood that within the scope of the appended claims the invention may be practiced otherwise than as specifically described.

That which is claimed is:

1. An apparatus for the defluorination of a liquid hydrocarbon mixture, containing organic fluorides, produced during the conversion of hydrocarbons using a fluorine-containing catalyst comprising:

a distillation column having a vertically elongated container, a first inlet for introducing said liquid hydrocarbon mixture into said elongated container, a series of vertically spaced trays within said container spaced above and below said first inlet, said trays suitable to allow countercurrent contact between upwardly flowing vapors and downwardly flowing liquid hydrocarbon mixture, a trap-out tray below said series of vertically spaced trays wherein said trap-out tray prevents further downward flow of said liquid hydrocarbon mixture in said container, a first outlet positioned in fluid flow communication with said trap-out tray so that said liquid hydrocarbon mixture can be removed from said elongated container, a second inlet located at the bottom of said container, for introducing a liquid effluent into said container, a contacting material located above said second inlet and below said trap-out tray, such that as liquid effluent enters through said second inlet, liquid effluent already in said bottom of said container flows through said contacting material, a second outlet in fluid communication with the contacting material for removing liquid effluent having flowed through said contacting material, and a third inlet located above said contacting material for introducing vaporous effluent into said container; and means for defluorinating said liquid hydrocarbon mixture in fluid flow communication with said first outlet, said second inlet, and said third inlet such that said means receives liquid hydrocarbon mixture from said first outlet, thermally decomposes at least a portion of said organic fluorides in said liquid hydrocarbon mixture forming a vaporous effluent containing hydrogen fluoride and leaving a liquid effluent, introduces said vaporous effluent to said third inlet, and introduces at least a first portion of said liquid effluent to said second inlet.

2. An apparatus according to claim 1 wherein said means for defluorinating comprises:

a heating means in fluid flow communication with said first outlet, for receiving liquid hydrocarbon mixture from said first outlet and heating said liquid hydrocarbon mixture to a suitable temperature for thermal decomposition of said organic fluorides to form a heated effluent containing said vaporous effluent and said liquid effluent; and a phase separation chamber in fluid flow communication with said heating means, said second inlet and said third inlet, for receiving said heated effluent and separating said vaporous effluent from said liquid effluent so that vaporous effluent is introduced to said third inlet and said first portion of said liquid effluent is introduced to said second inlet.

3. An apparatus according to claim 2 wherein said means for defluorinating further comprises means for removing a second portion of said liquid effluent from said phase separation chamber and for returning said second portion of said liquid effluent to said heating means for further thermal decomposition of said organic fluorides.

4. An apparatus according to claim 3 wherein said contacting material is activated carbon.

5. An apparatus for the defluorination of a liquid hydrocarbon mixture, containing organic fluorides, produced during the conversion of hydrocarbons using a fluorine-containing catalyst comprising:

a distillation column having a vertically elongated container, a first inlet for introducing said liquid hydrocarbon mixture, a series of vertically spaced trays within said container spaced above and below said first inlet, said trays suitable to allow countercurrent contact between upwardly flowing vapors and downwardly flowing liquid hydrocarbon mixture, a trap-out tray below said series of vertically spaced trays wherein said trap-out tray prevents further downward flow of said liquid hydrocarbon mixture in said container, a first outlet positioned in fluid flow communication with said trap-out tray so that liquid hydrocarbon mixture can be removed from said trap-out tray, a second inlet located at the bottom of said container, for introducing a liquid effluent into said container, a second outlet located below said trap-out tray for removing liquid effluent from said container, a third inlet located above said second outlet for introducing a vaporous effluent into said container;

a heating means having an inlet and an outlet, wherein said heating means inlet is in fluid flow communication with said first outlet so that said heating means receives liquid hydrocarbon from said first outlet and wherein said heating means heats said liquid hydrocarbon to a suitable temperature for thermal decomposition of said organic fluorides producing a heated effluent containing said vaporous effluent and said liquid effluent; and a phase separation chamber for separating said vaporous effluent from said liquid effluent, wherein said phase separation chamber is in fluid flow communication with said heating means outlet, said second inlet and said third inlet, so that it receives said heated effluent from said heating means outlet, separates said vaporous effluent from said liquid effluent, introduces said vaporous effluent to said third inlet, and introduces at least a first portion of said liquid effluent to said second inlet.

6. An apparatus according to claim 5 wherein said phase separation chamber is in fluid flow communication with said heating means inlet so that a second portion of said liquid effluent from said phase separation chamber is returned to said heating means for further thermal decomposition of organic fluorides.

7. An apparatus according to claim 6 further comprising a valve means located in fluid flow communication between said phase separation chamber and said heating means which is adapted to regulate flow of said second portion of said liquid effluent from said phase separation chamber to said heating means.

8. An apparatus according to claim 5 wherein said distillation column further comprises a contacting material located above said second inlet and below said second outlet, such that as said first portion of said liquid effluent enters through said second inlet, liquid effluent already in said bottom of said container flows through said contacting material and after liquid effluent flows through said contacting material, it is removed from said container through said second outlet.

9. An apparatus according to claim 7 wherein said contacting material is activated carbon.

10. An apparatus according to claim 5 further comprising a defluorinating chamber containing a contacting material wherein said defluorinating chamber receives said first portion of said liquid effluent from said phase separator such that said first portion of said liquid effluent flows through said contacting material to undergo further defluorination and thereafter flows to said second inlet.

* * * * *